United States Patent
Kuwana et al.

(12) 
(10) Patent No.: US 6,180,400 B1
(45) Date of Patent: *Jan. 30, 2001

(54) METHOD OF SUBCULTURING CULTURING AVIAN CELLS AT PH 7.8 OR ABOVE

(75) Inventors: Takashi Kuwana, Kumamoto; Koichiro Hashimoto; Akira Nakanishi, both of Kanagawa, all of (JP)

(73) Assignee: Meiji Milk Products, Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/793,770
(22) PCT Filed: Aug. 24, 1995
(86) PCT No.: PCT/JP95/01681
 § 371 Date: May 1, 1997
 § 102(e) Date: May 1, 1997
(87) PCT Pub. No.: WO96/06160
 PCT Pub. Date: Feb. 29, 1996

(30) Foreign Application Priority Data

Aug. 24, 1994 (JP) ................................................. 6/222429

(51) Int. Cl.⁷ ................................. C12N 5/02; C12N 5/00
(52) U.S. Cl. ........................... 435/325; 435/349; 435/375; 435/378; 435/395
(58) Field of Search ..................................... 435/325, 395, 435/349, 375, 378

(56) References Cited

PUBLICATIONS

Ramp et al., Bone and mineral, 24 (1), 1994, p. 59–73.*
Imbenotte et al., J. Cell Physiol., 124(2), 1985, 358–362.*
Asem et al., Domest, Anim. Endocrinol. 1984, 1(3), 235–249.*
DePomerai et al., Dev. Growth Differ. 23(6), 1981, p. 613–622.*
Rubin, H., J. Cell Physiol., 82(2), 1973, 231–238.*
Zacchei, A.M., Arch. Ital. Anat. Embriol., 66:36–62, 1961.*
Demain et al., Manual of Industrial Microbiology and Biotechnology, 1986, ASM, pp. 256–258.*
Cohn, A.E. and A.E. Mirsky (1929) "Physiological Ontogeny. A Chicken Embryos. XIV. The Hydrogen Ion Concentration Of The Blood Of Chicken Embryos As A Function Of Time" J. Gen. Physiuol. 12:463–468.
Nau, H. and J. Scott, Jr. (1986) "Weak acids may act as teratogen by accumulating in the basic milieu of the early mammalian embryo" Nature 323:276–278.
Tazawa, Hiroshi, T. Mikami and C. Yoshimoto (1971) "Respiratory properties of chicken embryonic blood during development" Respiration physiology 13:160–170.
Tazawa, Hiroshi, Tomohisa Mikami and Chiyoshi Yoshimoto (1971) "Effect Of Reducing The Shell Area On The Respiratory Properties Of Chicken Embryonic Blood" Respiration Physiology 13:352–360.
Tazawa, Hiroshi (1981) "Compensation Of Diffusive Respiratory Disturbances Of The Acid–Base Balance In The Chick Embryo" Comp. Biochem. Physiol., 69A:333–336.

* cited by examiner

*Primary Examiner*—Irene Marx
(74) *Attorney, Agent, or Firm*—Saliwanchik, Lloyd & Saliwanchik (57) ABSTRACT

A method of culturing avian cells in a medium with a pH value of 7.8 or above, whereby avian cells can be subcultured stably for long. Since avian cells have been incapable of subculture heretofore, it has been impossible to effect in vitro cell or gene manipulation therewith. Now that such a manipulation becomes possible by the invention method, the way is opened for the industrial utilization of avian cells in the creation of transgenic birds and the production of vaccines.

3 Claims, 10 Drawing Sheets

METHOD OF SUBCULTURING CULTURING AVIAN CELLS AT PH 7.8 OR ABOVE

This application was filed under 35 USC 371 as the national phase of PCT/JP95/01681 filed Aug. 24, 1995.

FIELD OF THE INVENTION

This invention relates to a method for culturing avian cells and cell lines that are obtained from said culture method.

BACKGROUND OF THE INVENTION

Since a "super-mouse" was created in 1982 by introducing a growth-hormone gene of a rat into a fertilized egg of a mouse (R. D. Palmiter et al.: Nature, 300, 611–615, 1982) and demonstrated that exogenous genes can be introduced into mammals, various attempts have been made to produce transgenic animals by introducing exogenous genes. Among such attempts, transgenic livestock are intensively produced to promote the improvement of breed, to provide donors for organ transplantation, and to construct animal factories that produce useful substances (bioreactors).

Especially, production of pharmaceutical and useful proteins by transgenic livestock should form a new field of industry for producing useful proteins since in animal cells sugar-chain modification that is indispensable for expressing pharmaceutical activities can be conducted in higher levels than in bacteria or yeast and since the cost for production of transgenic live stock and their maintenance is much lower than protein production in mass culture facilities for animal cells. Physiological effects of such useful proteins may be harmful for the animals that produces them. To eliminate such an adverse effect, attempts are made to secrete such products outside the body. Two practicable production systems are proposed.

The first system is production and secretion of useful proteins into the milk of a mammal. Implemented examples are a transgenic sheep which produces and secretes high concentrations of $\alpha$-1-antitrypsin in the milk (G. Wright et al.: Bio/Technology, 9, 830–834, 1991) and a transgenic goat which produces and secretes human tissue-type plasminogen activator in the milk (K. M. Ebert et al.: Bio/Technology, 9, 835–838, 1991).

The other system is production of useful substances into the albumen of an avian egg. Such a system with domestic fowls should be more useful than transgenic livestock since a large number of fowls can be kept under a closed and fully controlled environment, the generation interval is only half a year until sexual maturation, eggs are constantly obtained, and the breeding cost is much lower than the cost for raising livestock.

Three methods are presently used for introducing genes into avian fertilized eggs (embryos) to produce transgenic birds.

(1) Method for introducing genes by infecting blastoderm cells of a fertilized and oviposited egg of a fowl (the number of cells is already above 60,000) with retrovirus vectors to which genes to be introduced are connected. This method is now widely used. As the first transgenic chicken, Bosselman et al. obtained sperms of male that hatched from the eggs of which blastoderm cells were infected with avian retrovirus vectors lacking reproducing ability, and artificially fertilized a female with the sperms. And they confirmed that the vector DNA's were transmitted to their $F_1$ (Bosselman, R. A. et al.: Science, 243, 533–535, 1989).

(2) Method for obtaining transgenic birds by introducing genes into blastoderm cells of a oviposited egg, which are dissociated in advance with trypsin, injecting these cells into the subgerminal cavity of other blastoderm-stage eggs to create chimera birds, and crossing the chimeras. Since the technology to produce blastoderm chimera is already established (Petitte, J. N. et al.: Development, 108, 185–189, 1990), there should be a possibility of producing transgenic birds with this method if foreign genes could be introduced into injected cells.

(3) Method by microinjecting a gene into a one-cell-stage fertilized egg immediately after ovulation and externally cultivating the egg until it hatches. Unlike Methods (1) and (2), which introduce genes into blastoderm cells of eggs after oviposition, this method is only possible with the method developed by Perry et al. in 1988 for taking fertilized eggs out of a fowl immediately after ovulation and cultivating the egg until it develops into a chicken (Perry, M. M.: Nature, 331, 70–72, 1988). However, this method should be improved in many points to be used for producing transgenic fowls since it is difficult to inject genes into the nucleus or pronucleus because the nucleus of a fertilized egg is difficult to identify and the egg is polyspermy, and thus genes are mostly injected into the cytoplasm, producing a mosaic transgenic fowl.

Besides these methods, the method that injects genes into cells of the following types and produces chimeras should be useful for producing transgenic birds.

Corresponding cell types are 1) cells that exist within an embryo at the initial stage, such as blastoderm cells, primordial germ cells (PGC), and gonia (a general term for oogonia and spermatogonia), 2) embryonic stem cells (ES cells), which are cell lines established in vitro from blastoderm cells, and 3) embryonic germ cells (EG cells), which are cell lines derived from primordial germ cell gonia.

Since ES and EG cells keep growing without differentiating in vitro for a long period of time, it is possible to introduce genes into these cells under culture, select specific cell clones, produce germline chimeras with the technology for producing blastoderm chimeras, mutually cross the chimeras, and produce an animal that derives from an ES or EG cell. An ES cell lines that have the ability to form germline chimeras have been established for mouse (A. Bradley et al.: Nature, 309, 255, 1984). For birds, however, a cell line that may be ES has been reported to be established (WO93/23528) but the ability to form chimeras is not confirmed.

Since primordial germ cells and gonia, which develop into sperms or eggs, grow actively, gene manipulation is possible under culture as for ES cells if culture conditions for primordial germ cells and gonia are established. A report of a method for producing a fowl from primordial germ cells and gonia by transplanting these cells to another embryo (Kuwana, T. Jikken Igaku, Vol. 12, No.2 (special number), 260–265, 1994) suggests the possibility of producing transgenic birds from primordial germ cells and gonia.

EG cells were first established by Matsui et al. in mouse. Matsui et al. cultured the primordial germ cells of a mouse in the presence of stem cell factor (SCF), leukemia inhibitory factor (LIF), basic fibroblast growth factor (bFGF), and STO cells (Kawase et al., Jikken Igaku, Vol. 10, No. 13 (special number), 1575–1580, 1992) as feeder cells and established EG cell lines that was derived from the primordial germ cells, which formed colonies of the ES-cell-like morphology, grew, and had the ability to form chimeras (Matsui, Y., Zsebo, K. & Hogan, B. L. M.: Cell, 70: 841–847, 1992). This method may be applied to avian primordial germ cells to establish EG cell lines of birds.

These three types of cells either exist within an avian embryo or have been established from them. A method for stably and long culturing the cells from birds containing these cells in order to enable cell and gene manipulations, such as isolation of cells, establishment of cell lines and introduction of genes.

Prolonged passage cultures of avian cells may be used for producing vaccines for preventing virus diseases, such as Marek's disease of fowls. Cell culture is more appropriate for producing vaccines than fowl eggs since it can avoid contamination by other antigens.

However, avian cells could not be subcultured since cells grow and divide actively in the primary culture but stop growing and die several weeks after a number of vacuoles are observed within the cytoplasm of the cultured cells. Carrel reported that he succeeded in culturing for 34 years the connective tissue of a fowl embryo (Kuroda, Y., Dobutsu Soshiki Baiyo-ho, p. 2, Kyoritsu Shuppan k.k., 1974), but no one succeeded in confirming his experiment, which is now denied by the academic world. The fibroblast of fowl embryos was the only normal cells that can be subcultured for approximately 34 generations.

This invention aims to provide a method for stably and long culturing avian cells, especially cells of poultry such as domestic fowls and quails. The invention also aims to provide cell lines that are produced by avian cells cultured with this method.

DISCLOSURE OF THE INVENTION

The culture medium should be set at an appropriate pH range to achieve a successful animal cell culture, which should be equal to the pH of the in vivo environment of the cells. Usually, animal cells can grow at pH 6.8–7.6. The most appropriate pH was believed to be 7.2–7.4, and cells were believed to die within 24 hours under pH 6.6 or above 7.8.

The inventors, upon our attempt to successive and long culture avian embryo cells, which no person has succeeded in, selected the pH value of the blood among environment that surrounds developing embryo cells to determine the pH of the culture medium. However, the pH values of the blood of an initial-stage embryo have not been measured since it is difficult to collect sufficient amount of blood for measuring the pH.

Therefore, the inventors measured the pH values of blood along their development after embryos have developed enough to collect approximately 2 µl blood/embryo. The result, which was surprising, showed that the pH's of the blood were all 7.8 or above, the value where was believed that animal cells will die within 24 hours. Since embryo cells at their initial stages before blood circulation may be affected by the yolk and albumen, the pH values of the yolk and albumen next to the embryos were successively measured for reference.

The inventors concluded from the results that the comprehensive pH environment in which embryo cells grow primarily depends on the pH of the blood and that the pH of the blood is likely to be the most appropriate value for the cells to grow. The inventors cultured avian embryo cells in a medium that was set at above pH 7.8 and discovered that long passage culture was possible. The inventors applied said pH values to avian cells from a late-stage embryo, a young bird, and a matured bird, found that it is also possible to culture successively these cells for a long period of time, and completed this invention.

This invention provides 1) the method for culturing avian cells characterized by setting the pH of the culture medium at pH 7.8 or above and 2) avian cell lines produced by said culture method.

The following paragraphs describe the invention in detail.

To investigate the pH environment that surrounds avian embryo cells, the inventors selected domestic fowls and quails, which are the most popular poultry bred all over the world, as representatives of birds, and measured the pH values of the albumen and yolk that surrounded normally developing embryos and the pH values of the blood of the embryos along their development.

The pH value in a fowl embryo was approximately 8.5 at 47 hours incubation, when blood circulation began, was always above 8.0 until 108 hours incubation, and was above 7.8 hence after until it hatched. On the other hand, the pH of the albumen before blood circulation was even more basic (approximately pH 9.2–9.9), and the yolk was slightly more acidic (approximately pH 6.0–7.8). The location of embryo cells in a fertilized egg suggests that embryo cells at said development stage should be affected more by the albumen than by the yolk. The mixture of the albumen and yolk at this stage showed pH 7.8–8.0. Therefore, avian embryos should be under a very basic environment of pH above 7.8 even before the blood starts to circulate.

The above results revealed that the pH environment that surrounds embryo cells is always basic, at pH 7.8 or above.

The inventors cultured avian cells in a medium that was set at pH 7.8–8.2. Avian embryos were collected from fertilized and oviposited eggs of domestic fowls and quails by incubating said eggs in an incubator and taking out embryos at various development stages from the egg shell. The inventors succeeded in the passage culture of embryo cells for every developmental stages. Passage culture of heart cells and of gonad cells of a quail immediately after hatching was also successful with this method. All these cell cultures are stable and are still being cultured (they have been cultured for over 18 months). Culture medium of pH above 7.8 may be applied for cells of birds other than domestic fowls and quails, which have similar environments of embryo cells. Such a culture method which can successively culture avian cells for a long time is first discovered by the inventors.

Furthermore, the inventors improved greatly the in vitro survival rate by isolating the primordial germ cells of birds circulating in the blood before the cells migrated and settled into a primordial gonad and by culturing the cells with the method described above. Therefore, there is a higher possibility for conducting in vitro gene manipulation and developing them into an individual which have been impossible before for the primodial germ cells.

Unexpectedly, it was possible with this culture method to successive culture of cells other than those of birds, such as STO cell line derived from fibroblast of a mouse fetus and the human fibroblast cell line which already have been established, and a primary culture of cow aortic endothelial cells.

This method was proved to be effective for successive culture of mammalian cells besides avian cells. The embryos of oviparous animals other than birds that are oviposited enclosed in egg shell, such as reptiles, should be developing within a basic environment as avian embryos are, and should be able to be subcultured with the culture method of this invention.

As it is clear from the description above, this invention is characterized by setting of the pH of a culture medium for culturing avian cells at 7.8 or above, where was believed that animal cell would die within 24 hours.

Culture conditions other than pH such as temperature, osmotic pressure, nutrients, and components may correspond to the conventional conditions used for culturing mammalian cells or cells of avian embryos. Modification of these conditions is within the range that the person skilled in the art can conduct by systematically repeating experiments, and does not limit the range of this application.

The term "birds" in this invention includes poultry and other birds. Poultry, for example, includes domestic fowls, quails, domestic and wild ducks, geese, ostriches, turkeys, guinea fowls, pheasants, and so on.

The term "cell lines" in this invention includes not only cell lines in a narrow sense but also established cell lines, cell strains and clones.

As stated above, the characteristic of this invention is setting of a culture medium at pH 7.8 or above. An example of a use of this invention is given in detail in the following paragraphs, which by any means does not restrict the range of this invention.

The culture medium may be the Eagle's minimum essential medium (MEM), which was developed for propagating mouse L cells or human HeLa cells, or the 199 medium, which was developed to keep fibroblasts taken from a fowl embryo heart alive for a long time, supplemented with 5–10% fetal calf or chicken serum, 1–4 g/l of glucose to regulate osmotic pressure and to provide energy source, 10–30 mM HEPES (N-2-hydroxyethylpiperazine-N'-2-ethanesulfonic acid) or EPPS (N-2-hydroxyethylpiperazine-N'-3-propanesulfonic acid) to stabilize pH, and 0.05–0.1 mM of 2-mercaptoethanol. For cultures within the normal air, 2–4 g/l of $NaHCO_3$ is added to the medium, and the pH is adjusted with $Na_2CO_3$. Since the quality of the serum largely affects the growth of cells, each lot of the serum should be checked with the cells to be used. As $Ca^{++}$ is believed to be concerned in regulating cell growth and adhesion, approximately 1 mM of $Ca^{++}$ should be added. Components other than that given above may be selected for a medium when using this invention. However such selection is a routine technique that any person skilled in the art can conduct, and any medium set at pH 7.8 or above is included in this invention.

Culture temperature varies by species, and the temperature appropriate for each species may be selected. The temperature for avian embryo cells is usually 37°–38.5° C.

Passage culture is usually conducted in the following manner. When initially planted cells divide, grow, and cover ⅓ to ⅔ of the bottom surface of the culture container, the medium is removed. The cells are treated at 37° C. for 3–5 minutes with 0.05–0.1% trypsin and PBS(–) containing 0.02% EDTA (a balanced salt solution from which $Ca^{++}$ and $Mg^{++}$ are removed) to disperse cells. The cells are centrifugally collected, dispersed in a new medium solution, and counted. A certain concentration of the cell suspension medium is transferred into a new culture dish and cultured. Subsequent passage operations are conducted when the cells cover approximately 90% of the culture area. Culture solution is usually changed every 2 days.

Cultured cells may be freeze-preserved by suspending $10^5$–$10^6$/ml of cells in a growth medium containing 10% DMSO, putting the medium into 1 ml hard ampules, gradually freezing the cells by lowering the temperature at almost 1° C./minute until –80° C., and preserving the cells in liquid nitrogen. For a use, cells should rapidly be melted at 37° C., mixed with a growth medium, and centrifuged to remove the supernatant. The residual cells are cultured with the method described above.

Among the cell lines obtained with the long subculture method of this invention, a culture of cells from the area vasculosa of the lower half of a Stage-17 quail embryo, which was cultured for 29 generations, was deposited to the National Institute of Bioscience and Human-Technology, Agency of Industrial Science and Technology (accession number FERM P-14454).

BRIEF DESCRIPTION OF THE DRAWINGS

FIGS. 2-1 and 2-2 are phase-contrast microscopic photographs of the 8th subculture of the cells that were taken from the germinal crescent of fowl embryos at Stage 3–4 at a low and high magnifications, respectively.

FIGS. 3-1 and 3-2 are phase-contrast microscopic photographs of the 7th subculture of the cells that were taken from the germinal crescent of fowl embryos at Stage 3–5 at a low and high magnifications, respectively.

FIGS. 4-1 and 4-2 are phase-contrast microscopic photographs of the 24th subculture of the cells that were taken from the gonads of 4-day fowl embryos at a low and high magnifications, respectively.

FIGS. 5-1 and 5-2 are phase-contrast microscopic photographs of the 5th subculture of the cells that were taken from the germinal crescent of quail embryos at Stage 3–5 at a low and high magnifications, respectively.

FIGS. 6-1 and 6-2 are phase-contrast microscopic photographs of the 7th subculture of the cells that were taken from the primordial gonads of fowl embryos at Stage 17 at a low and high magnifications, respectively.

FIGS. 7-1 and 7-2 are phase-contrast microscopic photographs of the 24th subculture of the cells that were taken from the hearts of 7-day quail embryos at a low and high magnifications, respectively.

BEST MODE FOR CARRYING OUT THE INVENTION

This section gives an example of a use of this invention. This invention is not restricted by any means by such an example.

1. pH measurement

The pH's of the albumen, yolk and blood were measured for domestic fowls and quails to investigate the environment of embryo cells.

Domestic fowls used were White Leghorns, and quails were Japanese quails. Fertilized and oviposited eggs were incubated at 38.5° C., relative humidity 60%, in a forced air incubator (P-800, Showa Incubator Lab., Japan). Embryos at various developmental stages were collected. The developmental stages of domestic fowls are expressed in accordance with the table for developmental stages by Hamburger and Hamilton (Hamburger, V. and Hamilton, H. L., J. Morphol., 88: 49–92, 1951). The developmental stages of quails are usually expressed by "the stage table of Zacchei" (Zacchei, A. M., Archno Ital. Anat. Embryol. 66: 36–62, 1961), which is too rough to identify the developmental stages. This specification applied the "table for developmental stages by Hamburger and Hamilton" to quail embryos and notes the corresponding stages within brackets.

Blood was collected from embryos at Stages 12, 13, 14, 15, 16, 17, 18, and 25, 6-day embryo, 11-day embryo, and hatching chick. Aqueous albumen and yolk immediately beneath embryos were collected for embryos of every stages, from Stage 1 to hatching chick. Microcapillaries that were rinsed three times with diluted water were used to collect these specimens. The pH of the specimens of approximately 2 $\mu$l each were measured with a pHBOY-C1 (Shindengen) immediately after they were collected.

Figure 1:
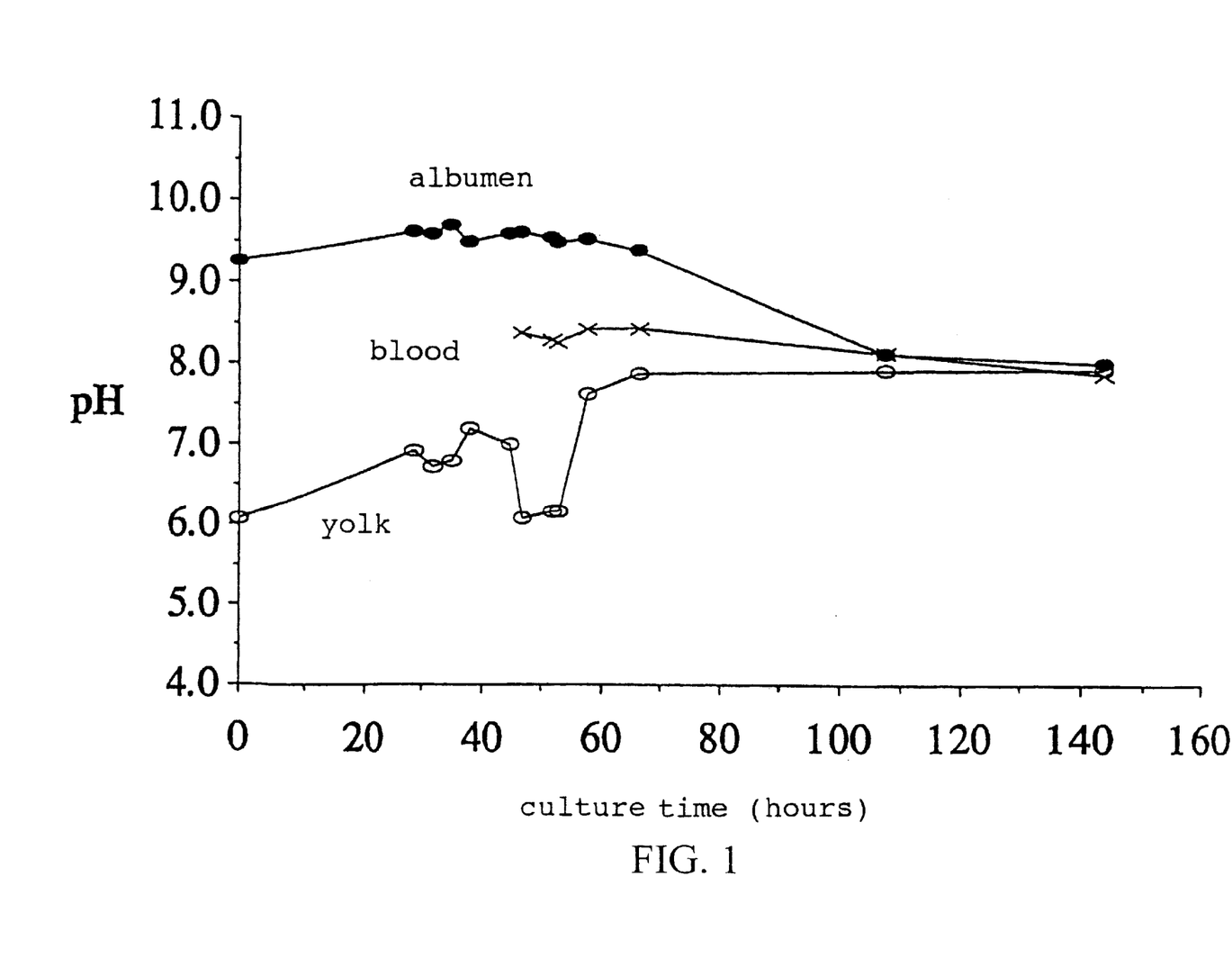
FIG. 1 shows the pH measurements for albumen, yolk and blood that surround a developing fowl embryo along the passage of time.

The pH measurements of blood, albumen that surrounds a fowl embryo, and yolk immediately beneath the embryo are shown in FIG. 1. In domestic fowls, blood is observable from 47 hours of incubation (Stage 12). The pH of the blood at this stage was approximately 8.5, was above 8.0 until 108 hours of incubation, and was above about 7.8 until hatching. Quails showed a similar tendency.

On the other hand, the pH environment of embryo cells before blood circulation (before Stage 11) may be determined by albumen and yolk. The pH of albumen during said stages was more basic than blood, and the pH of yolk was more acidic. As a whole, the pH environment in which embryo cells develop should be more basic than the pH of an ordinal culture medium for animal cells. The pH measurements of mixtures of albumen and yolk at this stage showed values between 7.8 and 8.0.

2. Culture of various types of cells 2.1 Cells

The culture method of this invention was used for culturing the following cells:

1 domestic fowl (White Leghorn)

germinal crescent of a Stage 3–4 embryo germinal crescent of a Stage 3–5 embryo primordial gonad and area vasculosa of a Stage 17 embryo gonad of a 4-day embryo (Stage 24)

heart and gonad of a 7-day embryo (Stage 31)

2 Japanese quail germinal crescent of a Stage 3–5 embryo (Zacchei's stage 1–3)

primordial gonad and area vasculosa of a Stage 17 embryo(Zacchei's stage 14)

heart and gonad of a 7-day embryo (Stage 31 or Zacchei's stage 22)

heart and testis of a chick immediately after hatching (male) (Stage 46 or Zacchei's stage 33)

3 established mouse cell lines

STO (fibroblasts)

SL-10 (subclone of STO)

ST-2

4 primary culture of cow cells aortic endothelial cells of cow 5 human fibroblasts cells that were collected from the dermal tissue of a forearm of a healthy Japanese man and that were cultured for 25 generations with Eagle-MEM medium with 10% fetal calf serum 2.2 Culture medium The composition of the culture medium (hereafter, culture medium for birds) was:

alpha-MEM (GIBCO BRL 11900-016, U.S.A.), supplemented with

D-glucose 1 mM, $CaCl_2$ 1 mM, 2-mercaptoethanol $5 \times 10^{-5}$M, $NaHCO_3$ 1.4 g/l, EPPS(N-2-Hydroxyethylpiperazine-N'-3-propanesulfonic acid) 10 mM, 5% fetal calf serum (JRH Bioscience, U.S.A.), and 5% chicken serum (JRH Bioscience, U.S.A.).

The pH of the medium was adjusted at 8.2 with $Na_2CO_3$ under a normal air.

2.3 Culture method

Within a phosphate buffer salt solution that did not contain $Ca^{++}$ or $Mg^{++}$ [PBS(−); pH 8.2], germinal crescent regions were isolated from Stage 3–4 and Stage 3–5 embryos of White Leghorn and Japanese quail, gonads and areas vasculosa were isolated from their Stage 17 embryos, gonads were isolated from 4-day fowl embryos, and gonads and hearts were extracted from their 7-day embryos, all as tissue pieces. Heart and testis were dissected from a quail chick immediately after hatching. The tissue pieces were quickly cut with a knife for iridotomy in fine pieces in a 35 mm petri dish that contained the culture medium for birds (0.5 ml). The fine pieces of tissues were put in plastic culture vessels (Corning, U.S.A., product number: No. 25102S) each with 5 ml of the culture medium for birds, and the vessels were tightly capped. The tissues were statically cultured, by exchanging the entire culture medium every 2 days.

Passage culture was conducted when cells occupied about 30% of the culture surface of the culture vessel by treating cells with PBS(−) that contained 0.1% trypsin and 0.02% EDTA to disperse the cells and by transplanting the cells into another vessels that contained new culture medium. Passage operations were conducted hence after when the culture cells occupied about 90% of the culture surface.

The established mouse cell lines and cow aortic endothelial cells were cultured with the culture medium for avian embryos and were subcultured with the method described above.

The human fibroblasts that were subcultured for 25 generations in Eagle-MEM culture medium with 10% fetal calf serum were cultured in the culture medium for birds with the method described above.

2.4 Results

All fowl and quail cells tested could be subcultured. FIGS. 2 to 7 are phase-contrast microscopic photographs of subcultures of fowl and quail embryo cells at low and high magnifications. Cells taken from fowl and quail embryos have been subcultured for 3–15 months and are still being subcultured.

FIG. 2 shows the photographs of the 8th subculture of cells that were taken from the germinal crescent of fowl embryos at Stage 3–4. FIG. 3 shows the photographs of the 7th subculture of cells that were taken from fowl embryos at Stage 3–5. FIG. 4 shows the photographs of the 24th subculture of cells that were taken from the gonads of 4-day fowl embryos. FIG. 5 shows the photographs of the 5th subculture of cells that were taken from the germinal crescent of Stage 3–5 quail embryos. FIG. 6 shows the photographs of the 7th subculture of cells that were taken from the gonads of Stage 17 quail embryos. FIG. 7 shows photographs of the 24th subculture of cells that were taken from the heart of a 7-day quail embryo.

For the established mouse cell lines, all lines tested were possible to subculture for 15 generations or more. It was possible to subculture cow aortic endothelial cells for at least 10 generations.

Figure 8:
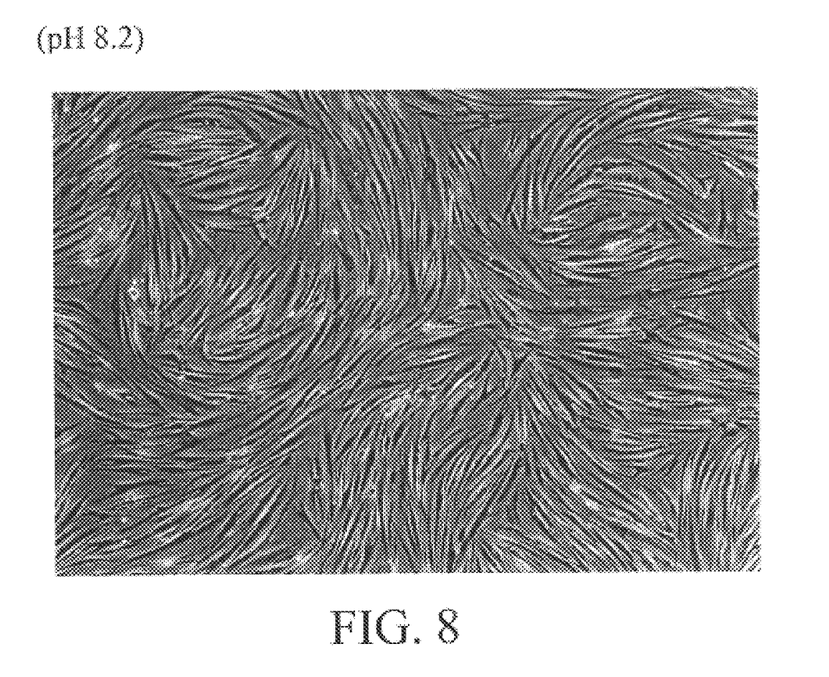
FIG. 8 is a phase-contrast microscopic photograph of the second subculture of human fibroblasts that were cultured with the method of this invention.
Figure 9:
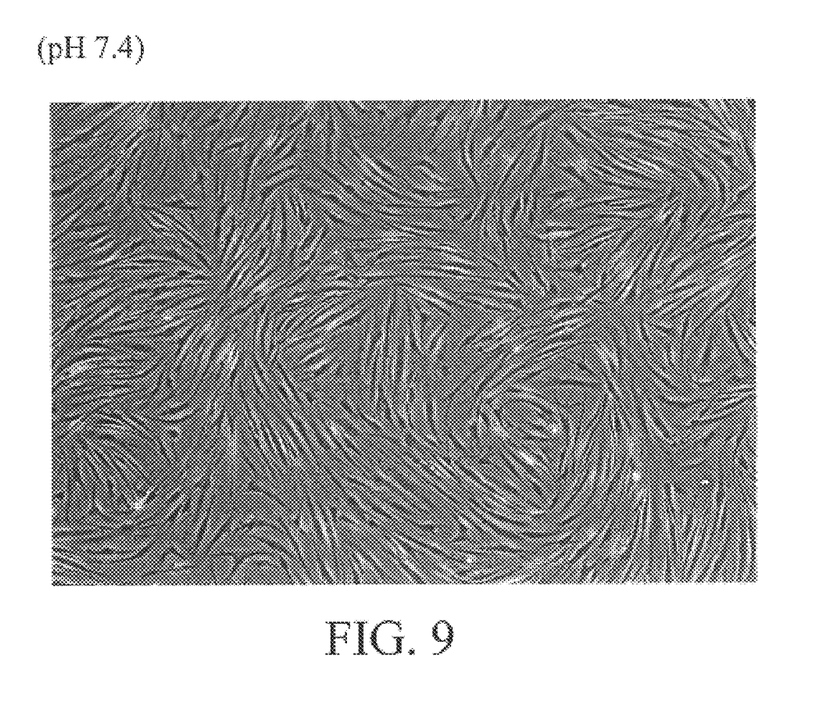
FIG. 9 is a phase-contrast microscopic photograph of the second subculture of human fibroblasts that were cultured with a conventional method.

Human fibroblast could be subcultured for 8 generations or more. A phase-contrast microscopic photograph of the second subculture of these cells that were cultured with the method of this invention is shown in FIG. 8. FIG. 9 shows a phase contrast microscopic photograph of the second subculture of the cells that were cultured with a conventional method for comparison with FIG. 8.

As these examples show, it is possible with the culture method of this invention to stably subculture avian cells for a long period of time, which was impossible with conventional culture methods. These examples showed that it is also possible to culture or subculture mammalian cells (both culture of established cell lines and primary culture). Especially, since STO and SL-10, which are used as feeder cells for establishing mouse ES or EG cell lines, can grow with the culture method of this invention, these cells may be used for establishing ES and EG cell lines from avian embryos. Furthermore, the culture method of this invention may be used for culturing and subculturing cells of other oviparous animals that deposit eggs covered with egg shell, such as reptiles.

3 Culture with various pH's 3.1 Cells

Cells from the germinal crescent (the region in which primordial germ cells are first recognized) of a Stage 3–5 fowl embryo were used.

3.2 Culture

Culture was conducted in culture vessels at 38.5° C., under 5% carbon dioxide and 95% normal air for pH 7.2 and under 100% normal air for pH 7.8.

The culture medium was alpha-MEM (GIBCO BRL 11900-016, U.S.A.) supplemented with

| | |
|---|---|
| D-glucose | 5.6 mM, |
| $CaCl_2$ | 0.81 mM, |
| $NaHCO_3$ | 16.7 mM, |
| $Na_2CO_3$ | 9.1 mM, |
| 2-mercaptoethanol | 50 μM, |
| EPPS (HEPES tor pH 7.2) | 10 mM, |
| 5% fetal calf serum (JRH Bioscience, U.S.A.), and | |
| 5% chicken serum (JRH Bioscience, U.S.A.). | |

The pH's of the culture medium was set at 7.2 (control) and 7.8 (experimental plot).

3.3 Results

Figure 10:
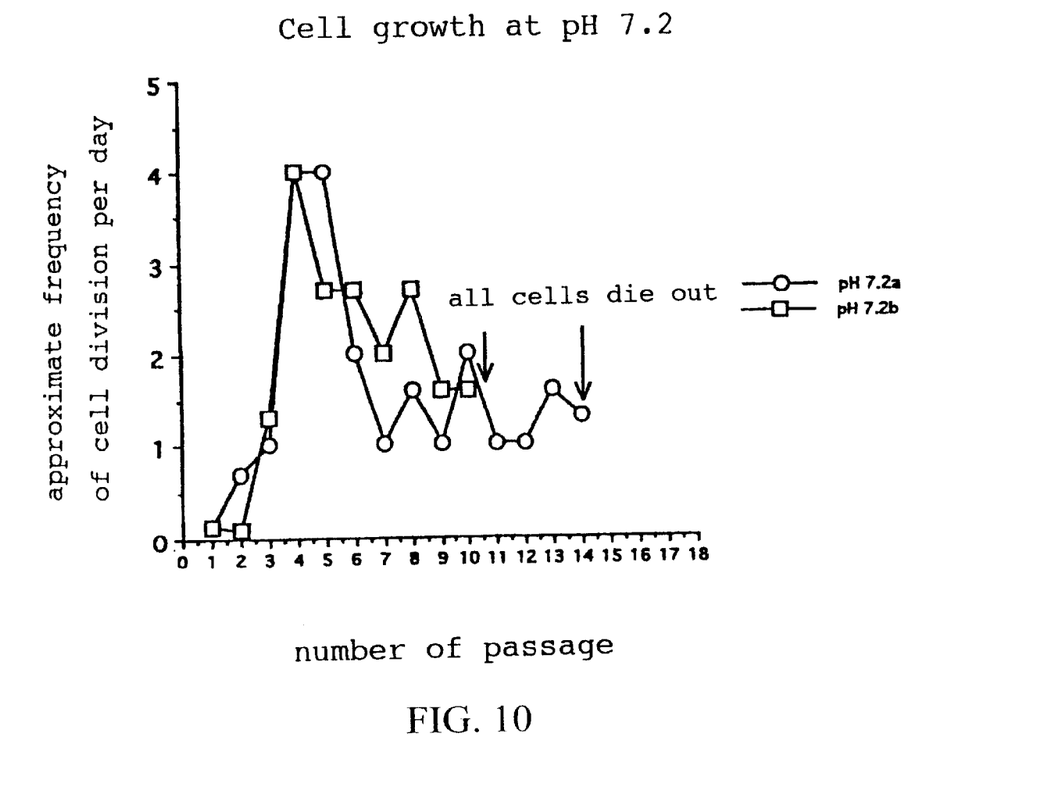
FIG. 10 shows the growth of cells that were taken from the germinal crescent of fowl embryos at stage 3–5 and cultured at pH 7.2.
Figure 11:
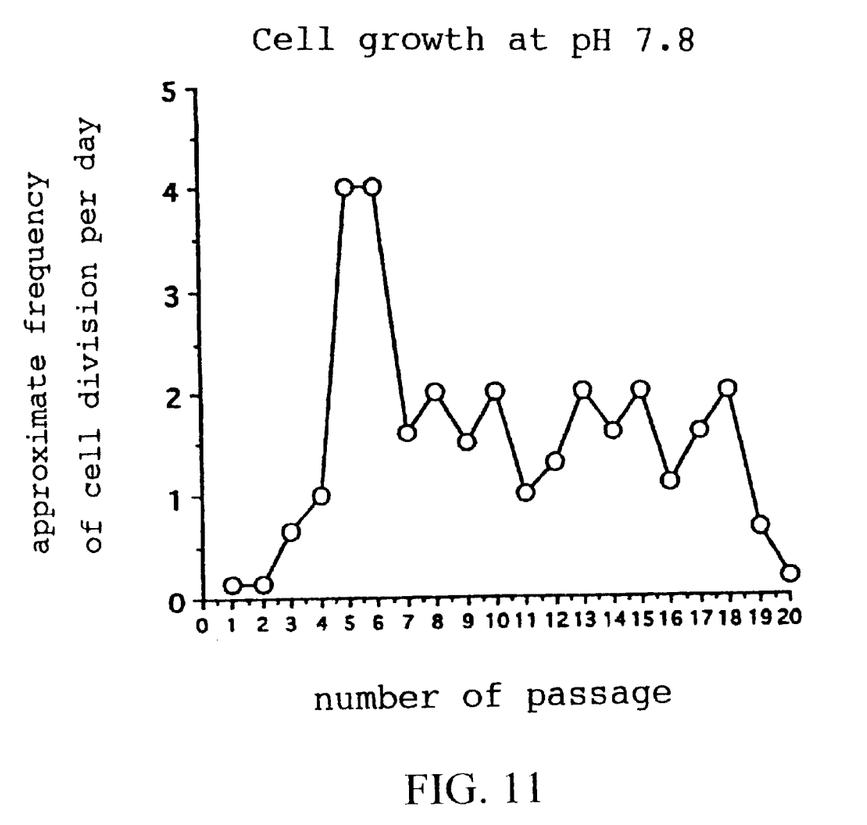
FIG. 11 shows the growth of cells that were taken from the germinal crescent of fowl embryos at Stage 3–5 and cultured at pH 7.8.
Figure 21:
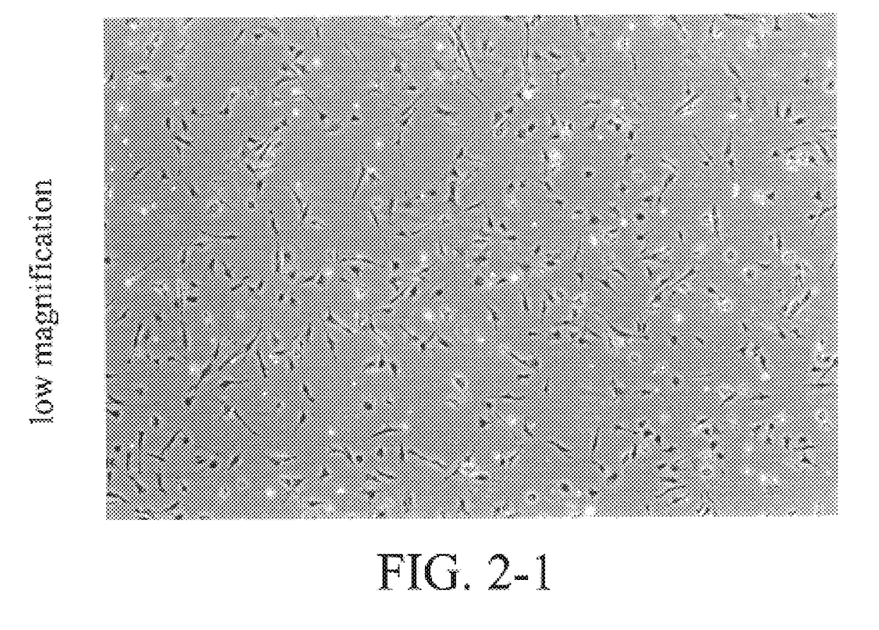
Figure 22:
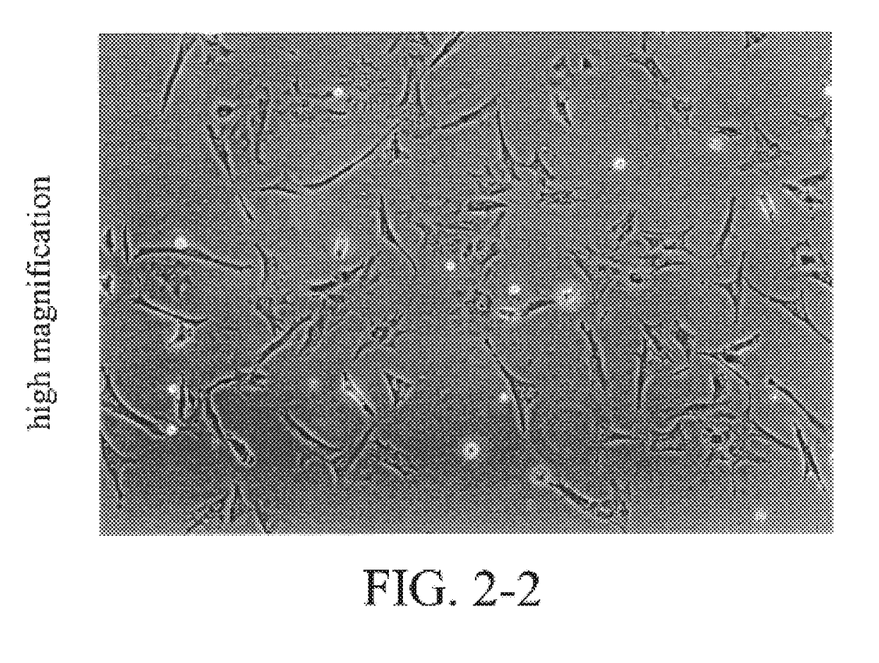
Figure 31:
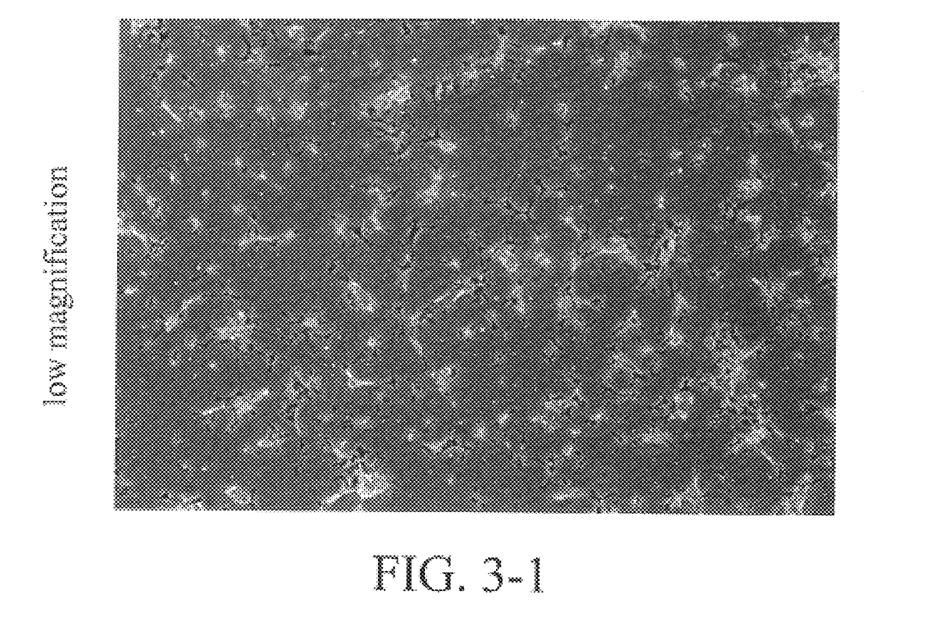
Figure 32:
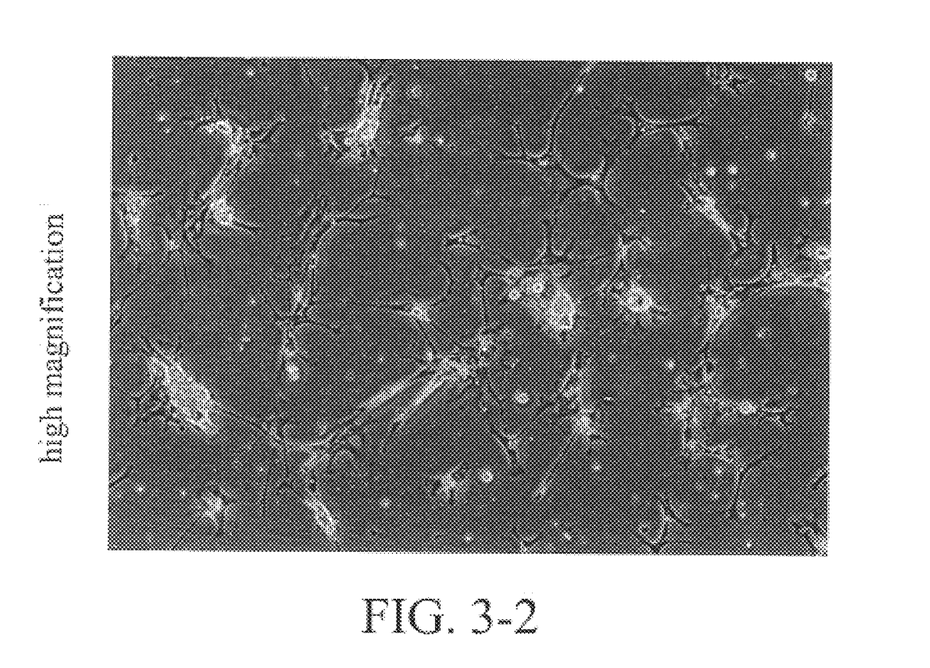
Figure 41:
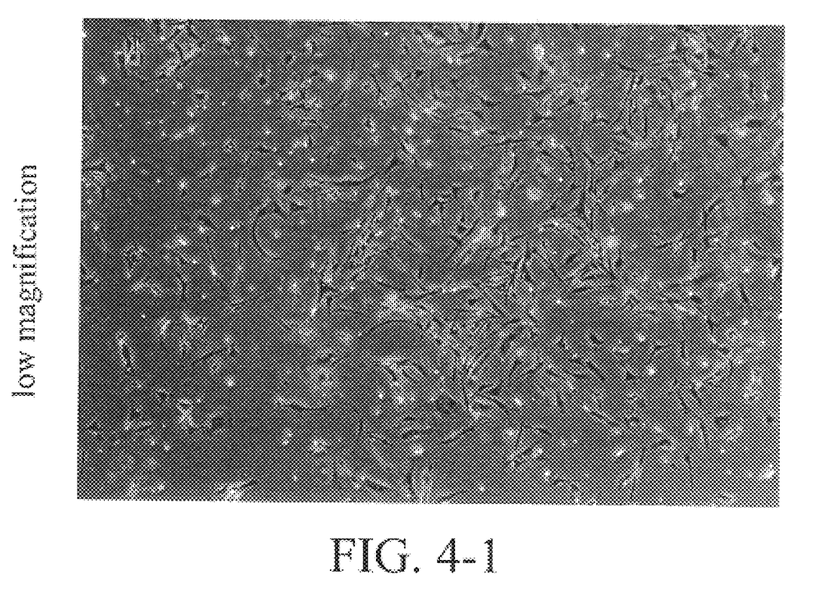
Figure 42:
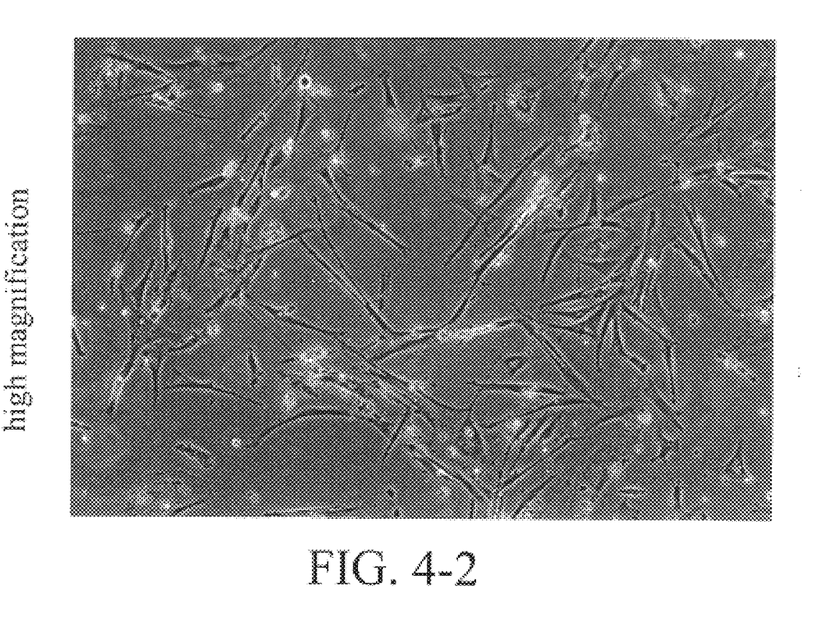
Figure 51:
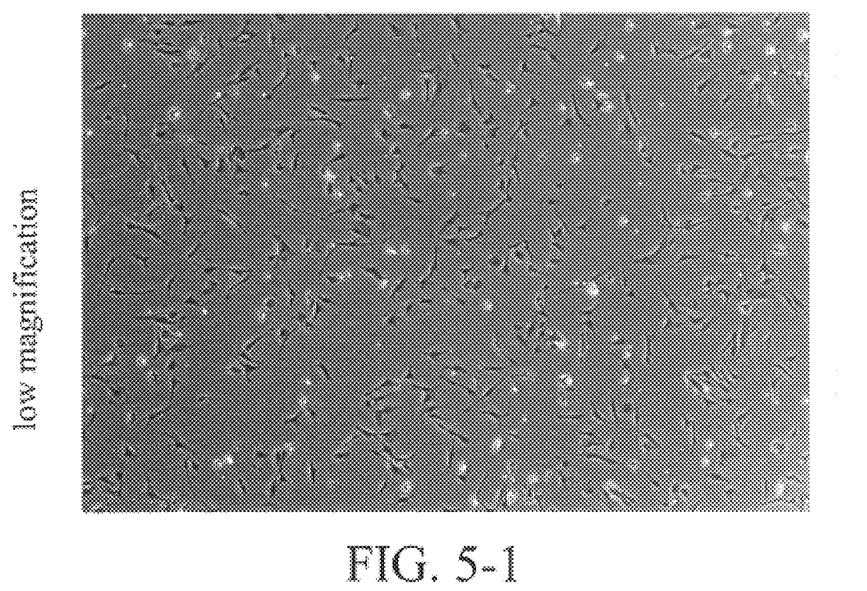
Figure 52:
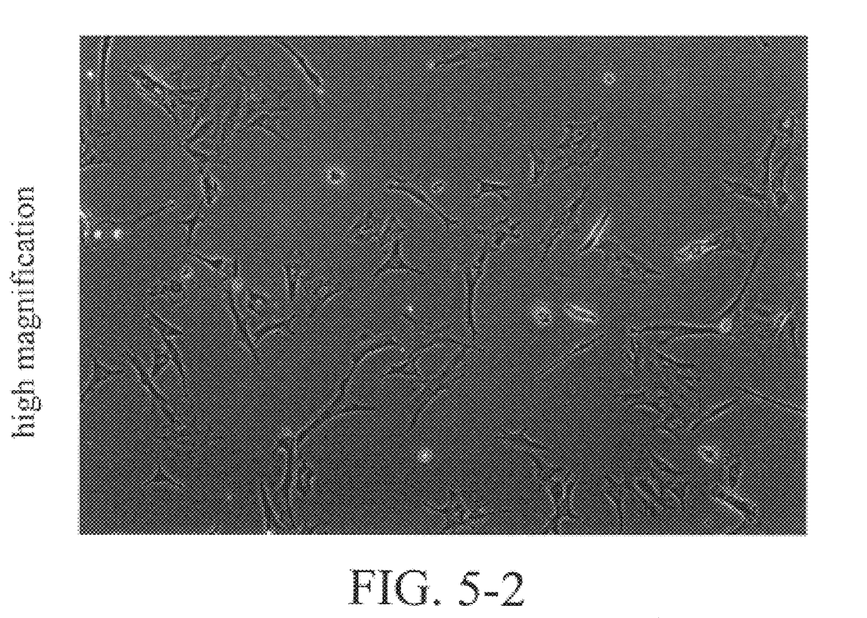
Figure 61:
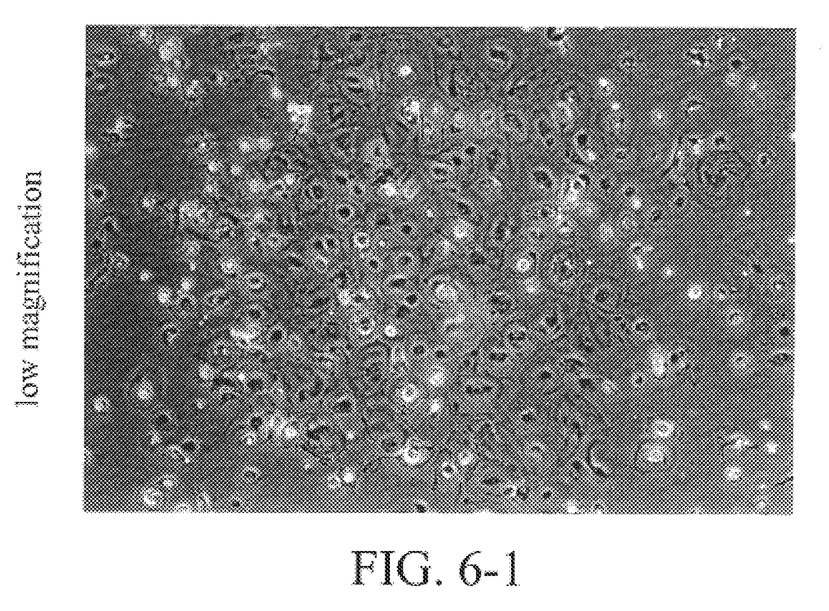
Figure 62:
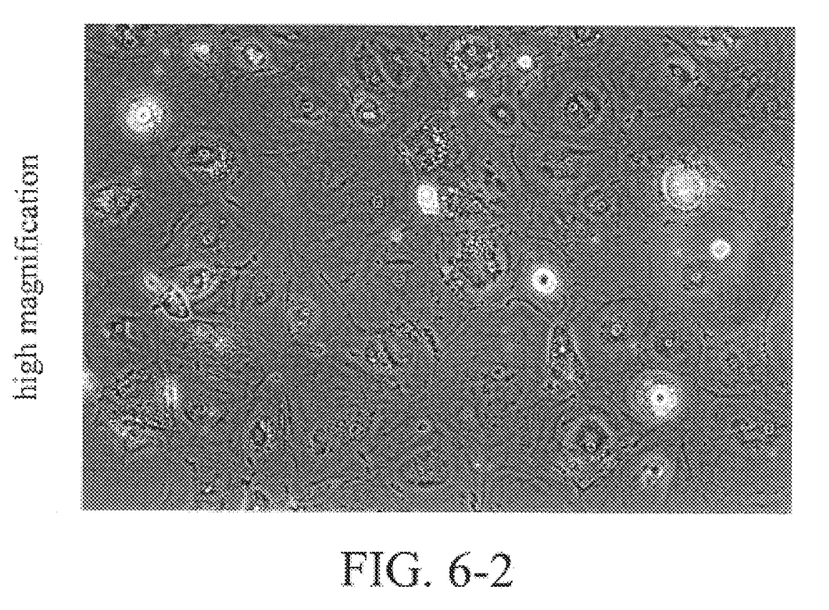
Figure 71:
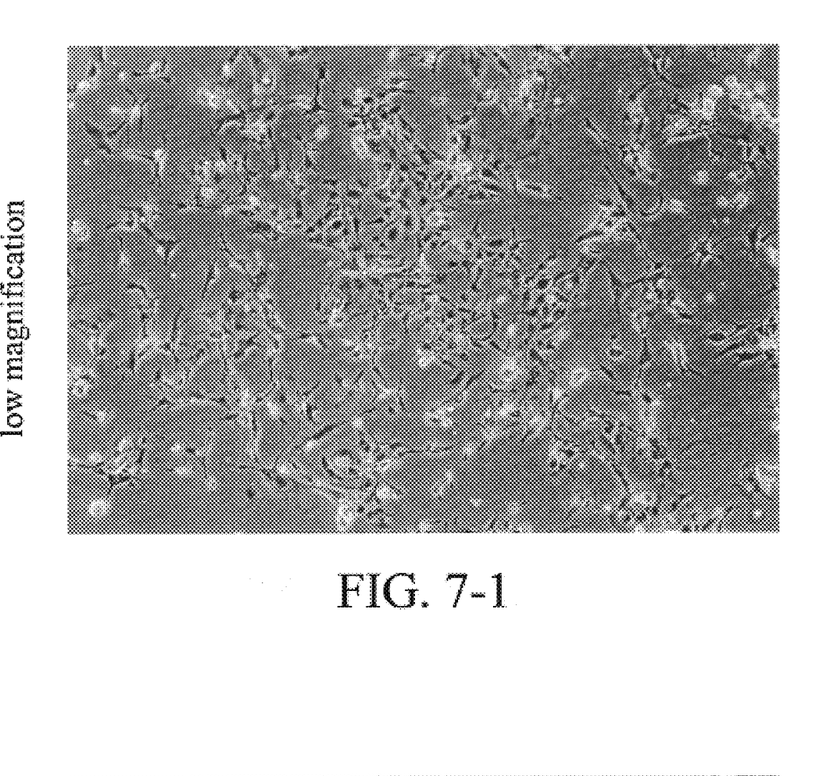
Figure 72:
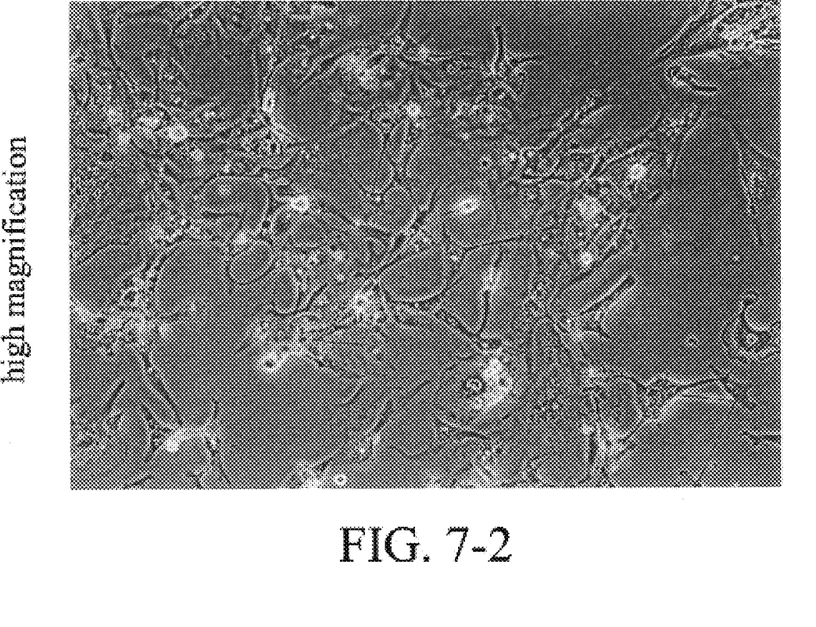

Results are shown in FIGS. 10 and 11. The horizontal axis shows the number of subculture, and the vertical axis shows the approximate number of cell division in one day. The values for the vertical axis were derived by dividing the dilution at passage by the number of days that was necessary for the cells to become confluent. These values are given as a convenient measure for showing the number and rate of cell division. These figures indicate that:

1) at pH 7.2, cells grew rapidly at the initial stage of culture, stopped dividing in 1–2 months, and died out (the "a" and "b" in FIG. 10 show two experiments conducted independently), and 2) at pH 7.8, cells showed a growth tendency similar to that in pH 7.2 but did not perish and could be subcultured. At pH 8.2, many cells died at the initial stage of culture, but it was possible to subculture cells that survived then.

4. Culture of primordial germ cells

Primordial germ cells of a developmental stage that has not reached primordial gonads were isolated from the blood of an embryo and cultured with both the conventional method and the method of this invention to compare the survival rates after a certain period of time.

4.1 Culture method

Fertilized eggs of domestic fowl (White Leghorn) were incubated at 80% humidity, 38.5° C., which in approximately 52 hours developed into Stage 13–15 embryos. Blood of approximately 3 μl was sampled with a glass microcapillary from a vessel of each embryo. About 200 μl of culture medium was mounted on a 35 mm plastic culture dish (Falcon, No.1008), on to which the blood was diffused. Under an inverted phase-contrast microscope, primordial germ cells were collected with glass microcapillaries and were separated from blood cells. Each 100 primordial germ cells were cultured with the culture medium for birds preset at pH 8.2 or pH 7.4 in 24-well multiplates for cell culture (Corning). The composition of the culture medium was equal to the culture medium for birds in application example 2. The shapes of the primordial germ cells were examined at 4 and 24 hours of incubation under an inverted phase-contrast microscope to compare the rate of cells with normal configuration. When 1) the surface of the cellular membrane was unclear, 2) blebbing has occurred, or 3) cellular destruction has apparently occurred, the cells are considered to be of abnormal configurations.

4.2 Results

The ratios of primordial germ cells that were estimated alive and kept their normal configurations after they were incubated for 4 hours at pH 7.4 and pH 8.2 were 6% and 94%, respectively. The ratios after 24 hours of incubation were 4% and 18%, respectively. These results indicate that the survival rate of primordial germ cells may be increased by raising the pH from 7.4 to 8.2. This demonstrates that the culture method of this invention may be effectively applied for developmental engineering operations that use primordial germ cells.

Industrial applicability

The culture method of this invention enabled prolonged and stable subculture of avian cells, which has been formerly impossible. The culture method of this invention opens the way for utilizing avian cells in industries, such as production of useful substances by utilizing transgenic technologies.

What is claimed is:

1. A method for subculturing embryonic avian cells comprising culturing said embryonic avian cells in a culture container comprising an initial culture medium having a pH of 7.8 or above, removing said cultured embryonic avian cells from the initial culture medium and placing said cultured embryonic avian cells in a new culture medium, pH of 7.8 or above and culturing said embryonic avian cells in the new culture medium, wherein said cultured embryonic avian cells derived from quail or chicken, remain viable for at least three months, grow on the surface of said culture container, and wherein said embryonic avian cells are optionally transferred one or more times to new culture medium.

2. The method for subculturing avian cells according to claim 1, wherein the pH of the culture medium is set between 7.8 and 8.2.

3. The method for subculturing avian cells according to claim 1, wherein said avian cells to cultured are cells derived from domestic quail.

\* \* \* \* \*

UNITED STATES PATENT AND TRADEMARK OFFICE
CERTIFICATE OF CORRECTION

PATENT NO. : 6,180,400 B1
DATED : January 30, 2001
INVENTOR(S) : Takashi Kuwana, Koichiro Hashimoto, Akira Nakanishi It is certified that error appears in the above-identified patent and that said Letters Patent is hereby corrected as shown below:

Title page (54)
Column 1,
Lines 1-2: "METHOD OF SUBCULTURING AVIAN CELLS AT PH 7.8 OR ABOVE"

should read

-- METHOD FOR CULTURING AVIAN CELLS AND CELL LINES OBTAINED THEREBY --

Signed and Sealed this

Twenty-first Day of August, 2001

Attest:

*Nicholas P. Godici*

*Attesting Officer*

NICHOLAS P. GODICI
*Acting Director of the United States Patent and Trademark Office*